United States Patent [19]
Feichtner et al.

[11] Patent Number: 5,430,308
[45] Date of Patent: Jul. 4, 1995

[54] 3-DIMENSIONAL RADIATION DOSIMETER

[75] Inventors: John D. Feichtner, Los Altos Hills; Joseph G. Depp, San Jose, both of Calif.

[73] Assignee: Accuray, Inc., Santa Clara, Calif.

[21] Appl. No.: 143,822

[22] Filed: Oct. 27, 1993

[51] Int. Cl.⁶ .............................................. G03B 42/02
[52] U.S. Cl. .................... 250/580; 250/475.2; 378/207
[58] Field of Search ............ 250/580, 583, 475.2; 378/208, 174, 207, 65, 68

[56] References Cited

U.S. PATENT DOCUMENTS

| | | | |
|---|---|---|---|
| 4,394,737 | 7/1983 | Komaki et al. | 250/580 X |
| 5,207,223 | 5/1993 | Adler | 128/653.1 |

FOREIGN PATENT DOCUMENTS 1450144  1/1989  U.S.S.R. ............................ 250/475.2

Primary Examiner—Constantine Hannaher
Assistant Examiner—Edward J. Glick
Attorney, Agent, or Firm—Gray Cary Ware & Freidenrich

[57] ABSTRACT

A three-dimensional dosimetry system and method for calibrating and mapping the expected radiation dose to be applied to a particular volume of tissue. In one embodiment, a stack of film is positioned within a radiation generation apparatus and is exposed to radiation. The film is scanned by a scanner and the scanner output is sent to a computer where it is compared to reference data of the desired dose distribution.

22 Claims, 6 Drawing Sheets

FIG. 5
HYPOTHETICAL SCANNER FOR DOSIMETRY PLATES
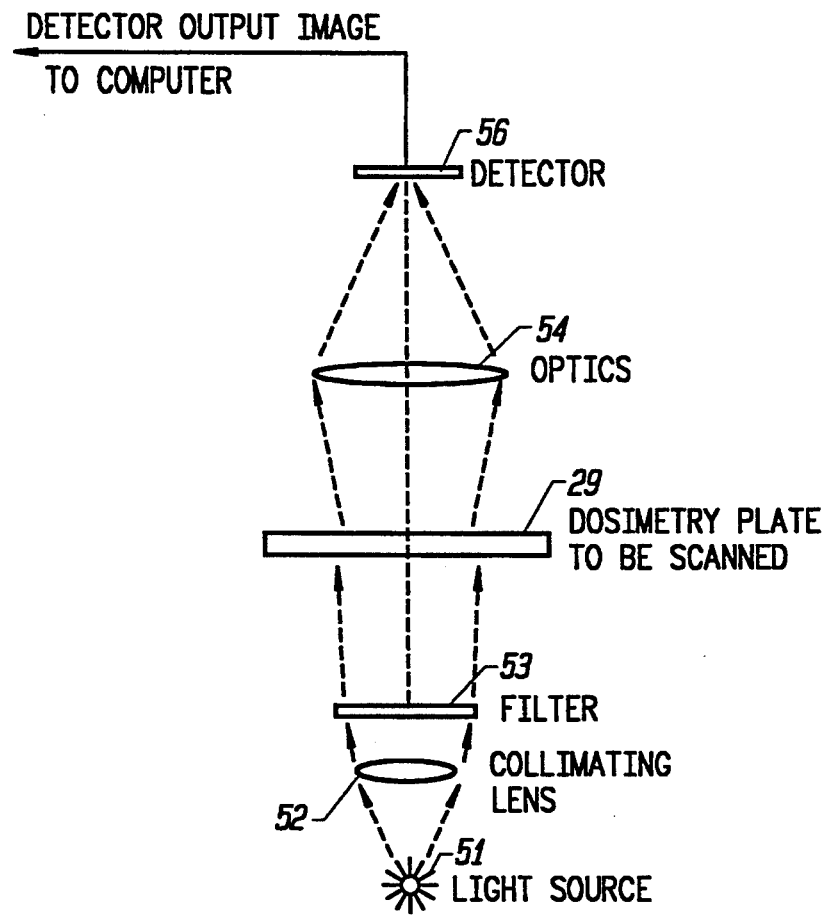
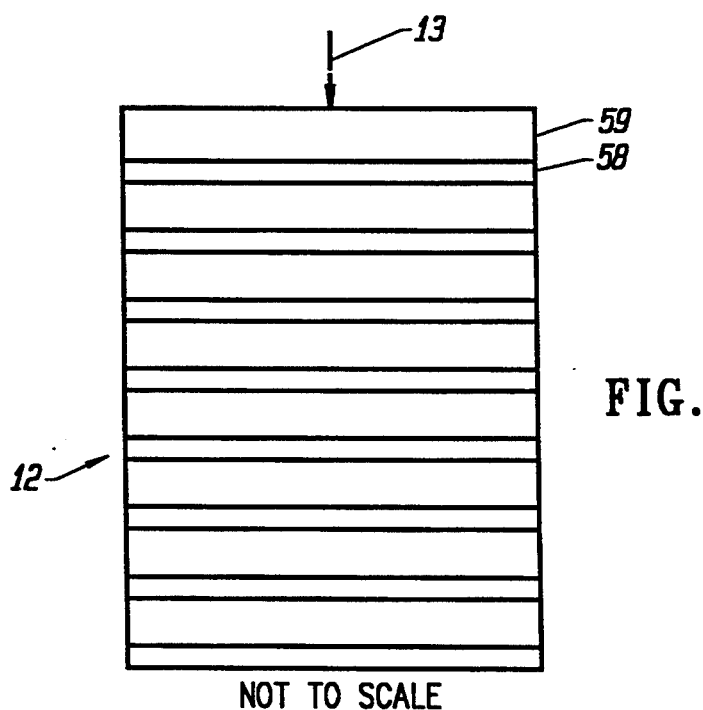
FIG. 6
NOT TO SCALE

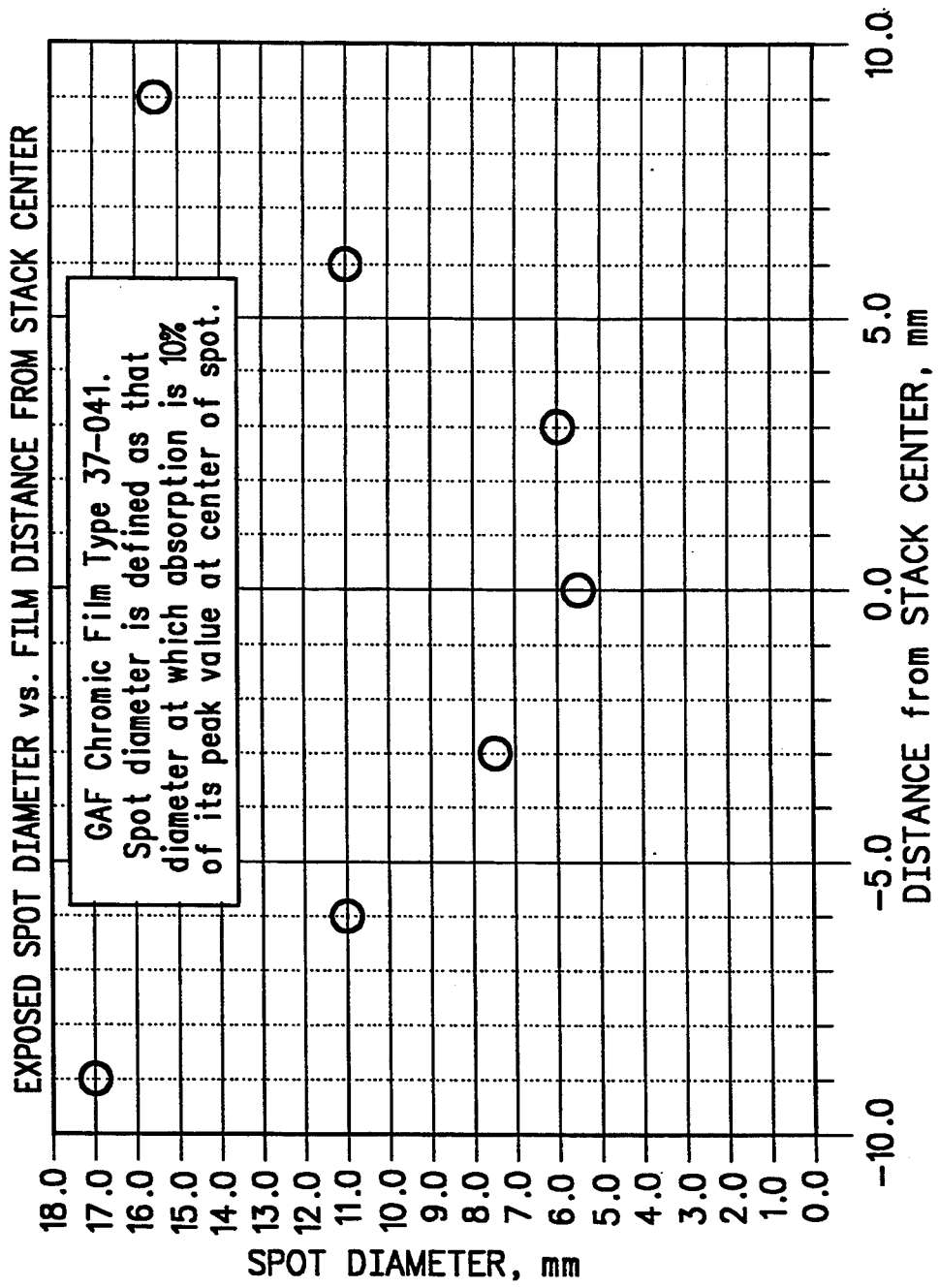

3-DIMENSIONAL RADIATION DOSIMETER

FIELD OF THE INVENTION

The present invention relates to a system and method used in preparation for stereotaxic surgery, and more particularly, to a system and method for testing on a model the three-dimensional radiation dose distribution resulting from stereotaxic surgical maneuvers.

BACKGROUND OF THE INVENTION

The use of stereotaxic radiosurgery to render tissue, and particularly tumorous tissue, necrotic is well known. While the radiosurgical principle of confining radiation as much as possible only to a particular volume is particularly attractive, problems regarding the precision of stereotaxic surgery remain an issue. With a risk that is proportional to both dose and the volume irradiated, radiation necrosis of tissue adjacent to a treated lesion remains the major complication of stereotaxic radiosurgery. Particularly, concerns remain as to whether particular volumes of tissue receive too much or too little radiation according to the prescription for treatment.

In stereotaxic radiosurgery, an accurate three-dimensional model of the skull or other tumor bearing portion of the body is generated from thin-cut CT scans, thus the volume requiring treatment can be visualized in three dimensions. A collimated radiation source is positioned in a sequence calculated to localize the energy deposition into a volume that as closely as possible conforms to that requiring treatment, while avoiding exposure of nearby healthy tissue. A system and method for performing stereotaxic surgery is disclosed in U.S. Pat. No. 5,207,223 issued to Adler on May 4, 1993 which is incorporated by reference herein. While this reference describes stereotaxic radiosurgery in which the treatment volume is accurately defined by moving the gamma beam in precisely defined arcs about the center of that volume, under that systems, the dose distribution is not defined or calibrated.

The dose distribution is an important parameter in stereotaxic surgery. If a radiation dose were too low due to unforeseen conditions at a point intended to receive the maximum radiation, then the surgery could be ineffective. If a radiation dose were too high at a particular point in the tissue, the surgery might have negative effects. Whether fixed or frameless stereotaxic radiosurgery is used, in order to determine if a particular scheme for the application of radiation beams to the tissue will result in a dose distribution within the prescribed limits and thereby optimize the treatment and minimize damage to healthy tissue, a system and method for such a determination is necessary. Thus, a system and method of calibrating and mapping the expected three-dimensional dose distribution that will be delivered by the collimated beam is desirable.

SUMMARY OF THE INVENTION

The present invention is a system and a method for calibrating and mapping the expected three-dimensional radiation dose to be applied to particular volume of tissue. In a computer memory, reference data representative of said particular volume of tissue is stored. Such reference data is, for example, the result of a CT scan.

The testing system of the present invention includes an apparatus for the application of directable radiation to a stack of individual films. The stack of films occupy a particular volume intended to represent the tissue of a patient. The source of the radiation is programmed to focus the directable radiation onto a particular test volume according to the prescribed treatment. The films receive the focused radiation and thus become exposed.

The films are then individually removed from the stack and scanned by a scanner. The image output from the scanner is sent to the computer where a comparison is made between the reference data and the scanner output. The outcome of the comparison will provide valuable information with respect to target accuracy and dose distribution. Upon inspection of the comparison, adjustments can be made to the radiation output prior to its application to a living subject.

BRIEF DESCRIPTION OF THE DRAWINGS

FIG. 5 shows the optical configuration of the scanner of the present invention;

FIG. 6 shows a stack of film according to the present invention; and

FIG. 7 shows a plot of exposure dimensions versus relative film position.

DETAILED DESCRIPTION OF THE INVENTION

In frameless stereotaxic radiosurgery as described in the above cited reference, the treatment volume is accurately defined by moving a gamma beam or x-ray beam (each used interchangeably throughout) in precisely defined arcs about the center of the volume. While the arc motion is not required according to the present invention, such a configuration is illustrative to visualize the essence of targeted collimated beam radiation treatment.

Figure 1:
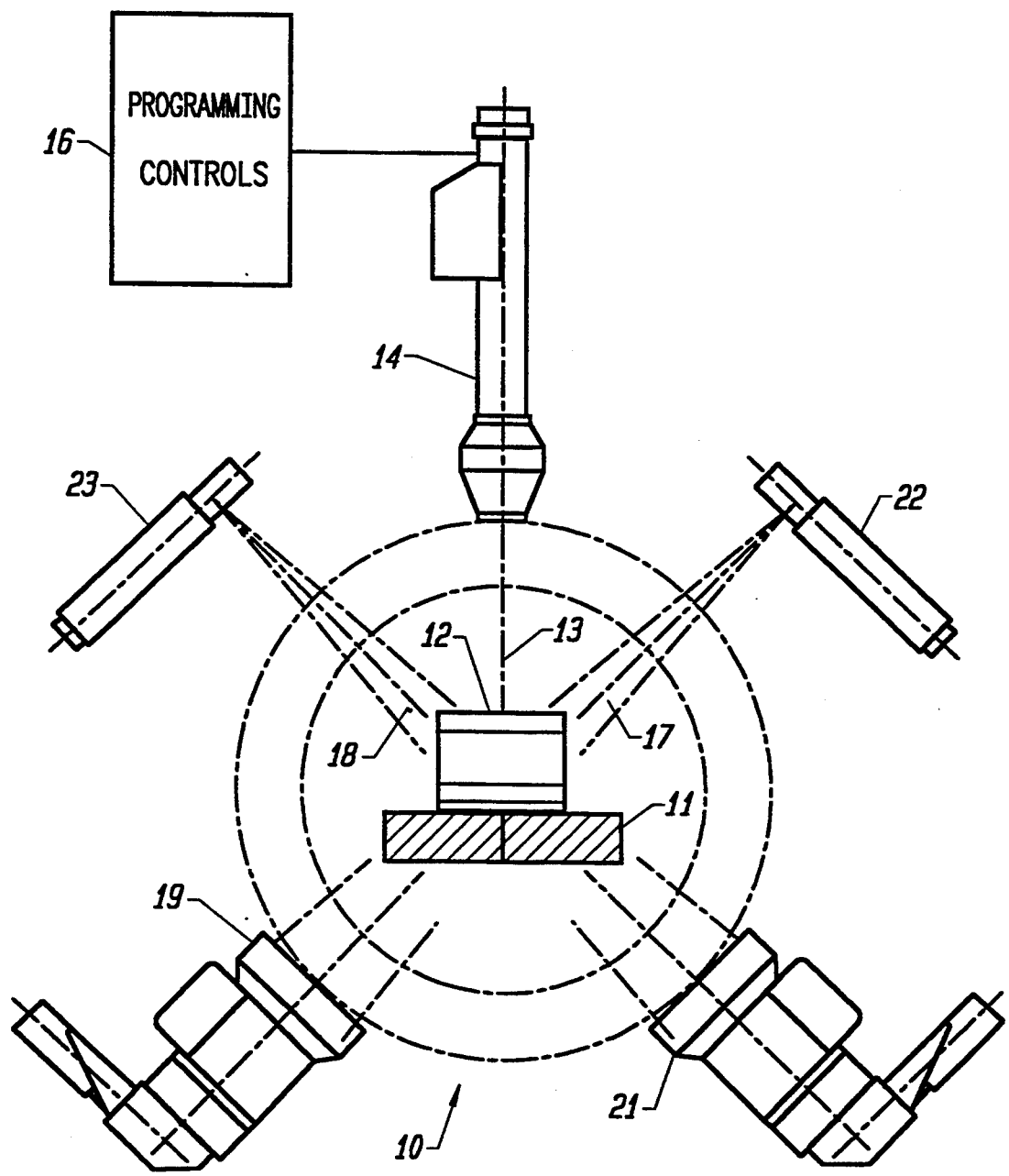
FIG. 1 illustrates, schematically, diagnostic x-ray imaging and directable radiation focusing aspects onto a film stack in accordance with the present invention.

In FIG. 1, a testing apparatus 10 of the present invention includes an apparatus similar to that shown in U.S. Pat. No. 5,207,223 issued to Adler on May 4, 1993. An operating table 11 accurately positions the stack of film 12 so that it receives the collimated beam 13 from beaming apparatus 14 which is programmed according to the programming controls 16 also described in detail in the above cited reference which, as discussed, is incorporated herein. The testing apparatus includes diagnostic beams 17 and 18, which are generated by a pair of x-ray generators 22 and 23. Appropriate image receivers 19 and 21 serve to produce electronic images representative of the first and second images of the respective first and second projections within the film stack 12 volume. The electronic images are passed to computational apparatus (not shown) so that the position of the beaming apparatus 14 is adjusted to assure that the collimated surgical beam which it produces is focused on the target region of the film stack 12 volume which is being irradiated.

The stack of film 12 to be irradiated occupies a particular volume which resembles the tissue of the patient within the testing apparatus 10. If desired, the stack of film can be placed inside a "phantom" housing, such resembling the shape of a human head. The phantom is constructed of a material such as polystyrene which is transparent to the directed radiation, thus allowing the radiation to pass therethrough to the stack of film.

The stack of film includes individual films or film plates which are radiochromic dye doped or impregnated plastic which are stacked in a packet arrangement. A film plate, for example, includes a thin film of radiation sensitive material called the "sensitive layer" is formed on a substrate which is typically less than 1 mm thick depending upon the film type used. In one embodiment of the present invention, the film is sandwiched between two layers of radiation transparent material such as polystyrene and then stacked in layers. As will be discussed in more detail below, in a preferred embodiment, the sensitive layer is deposited on a substrate which is 0.5 mm to 5 mm thick to facilitate stack handling and optimize exposure. The exposure of the film to the gamma beam 13 induces optical absorption in specific wavelength bands. Thus, only exposure to the gamma beam is required and no development needs to take place.

Figure 2:
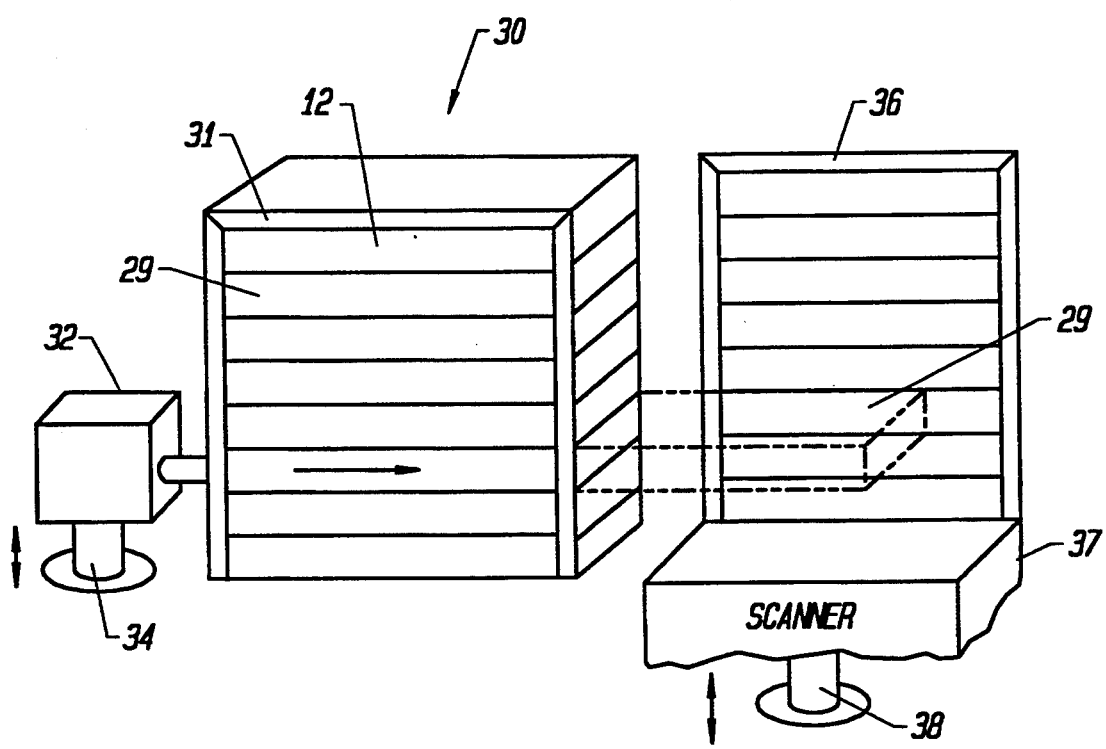
FIG. 2 shows the stack handler apparatus of the present invention.

Individual films 29 are arranged so that they are either positioned within the testing apparatus 10 in the stack handler or are subsequently positioned in the stack handler after they have been exposed. The stack handler is depicted in FIG. 2. generally by numeral 30. The stack handler 30 of the present invention removes individual film plates from the stack 12 so that the image exposed thereon is converted into scan data for transmission to the computer for comparison with the reference data.

In the configuration shown in FIG. 2, the stack handler 30 holds the film stack 12 within frame 31. A stack handler position lever 32 in this configuration is moved in the vertical direction by moveable lever support 34 to position it next to the film plate to be removed from the stack. The position lever 32 removes individual film plates from the stack by pushing them through the frame into a second frame 36 (half of which is depicted in FIG. 2). The second frame 36 holds the individual film plate 29 in position and the scanner 37 is moved in the vertical direction by moveable scanner support 38 to meet the film plate. Once scanned, either the film can be returned to frame 31 or moved into a different frame (see FIG. 4). The present invention also includes any other automatic delamination configuration including means by which a stack of film 12 is substantially securely stacked in a stacked arrangement and means for separating, removing and positioning the individual film plates so that the films can be scanned by a scanner after exposure.

Figure 3:
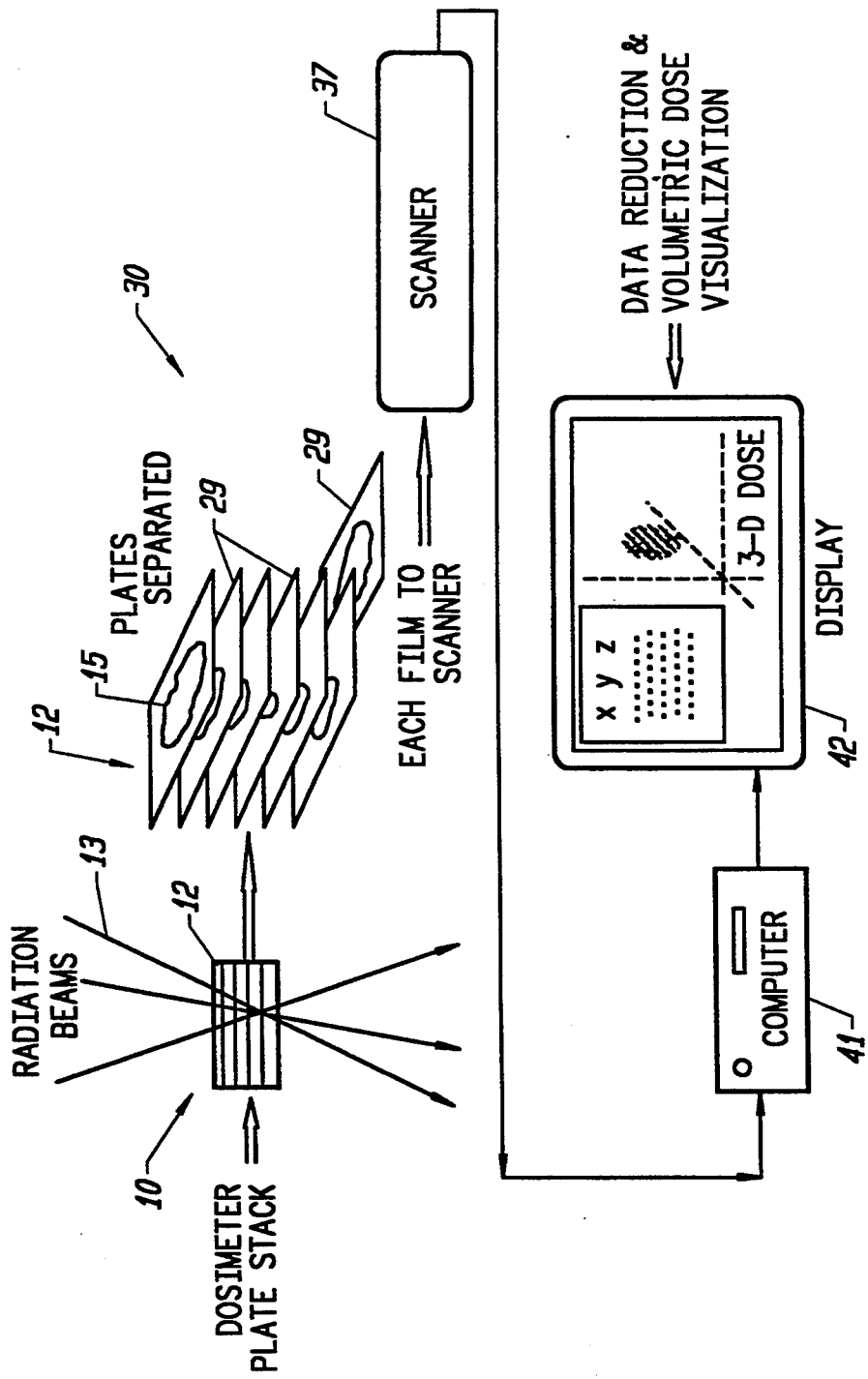
FIG. 3 shows a functional diagram of the present invention.

The testing apparatus of the present invention 10 is functionally depicted in FIG. 3. Again, the stack of film 12 is shown being exposed to radiation beams 13. The stack of film 12 is separated into separate film plates. Different images 15 on some or all of the individual film plates 29 is shown in FIG. 3. These images combined represent a three-dimensional model of a particular volume. Each of the film plates is sent to scanner 37. Once the film is scanned, the scanner output is sent to a computer 41. There the scanned information and the original reference data are compared. Upon data reduction, an optical image is displayed by screen 42 is generated depicting the actual dose distribution as compared with the desired dose distribution. The comparison can be rendered in any one of many known manners such as graphically or according to a table.

The film used according to the present invention is one in which the ratio of optical density generated in a particular band to that in the guard band gives the dose at a particular point on the film. In other words, after exposure an image representing the dose of radiation received at a particular location on the film is optically visible. The measured optical density at the location is proportional to the beam dosage received at that location. Since the three dimensional volume of the irradiated region is easily separated into planar slices and because the film exposure is immediate upon irradiation, the irradiation image can be scanned nearly immediately after the planar images are created.

In a preferred embodiment, the radiochromic film such as GAF Chromic type 37-040, 37-041 and Type FWT-60 available from Far West Technologies are useful when the collimated beam is low to high energy x-rays. The doses detectable therefore are 0.01 kGray to 50 kGray. Other types of film can also be used in accordance with the present invention. For example, when using low energy x-ray, silver halide photographic film such as that available from Kodak under the name X-omat V will provide exposures when the beam dose is between 0 and 10 Gray. Other types of film, include, for example, dyed plastic dosimetry plates of nylon, red or amber perspex, malachite green in poly (4-chlorostyrene). Also, undyed plastic films can be used such as cellulose triacetate and PMMA (polymethyl methacrylate). Also, Fricke gel-films or gels provide exposures up to 400 Gray. Moreover, color center formation in various salts (e.g. Lithium Fluoride) can be used. Dosimeter plates made of pure LiF crystals or other salts containing LiF will provide exposures from beam doses of 1000 to 10 million Gray. Furthermore, with respect to most if not all of the above mentioned film possibilities, different beam sources can be used. For example, electron beams having energies from 0.01 to 20 Mev and Gamma ray beams ($^{60}$Co, $^{192}$Ir, $^{137}$Cs) having energies from 0.1 to 4 Mev can be used. Under more particular circumstances, other forms of radiation can be used such as ultraviolet light beams or visible and near infrared light beams when silver halide film is used and when film absorption coefficient is low at the UV to IR wavelengths to be measured. Dose distributions from ion beams can be measured using thin films of photoresist.

Film thickness uniformity is a parameter which should be considered for accurate dosimetric readings. The fractional uncertainty in a measured dose is proportional to the sum of the fractional uncertainty of measuring the change in the absorption coefficient, $\Delta\delta$, plus the fractional uncertainty in the film thickness:

$$\Delta(Dose)/Dose = \Delta(\Delta\alpha)/(\Delta\alpha) + (\Delta t)/t.$$

Thus, for the total dose measured with a 1 mm thick film, the film thickness should be known over its area (or held constant) to within ±1% in order to yield a ±1% accuracy in dose. The film thickness of 1 mm, therefore, should be controlled to within ±10 micron over its area which, for example, is 5 cm×5 cm or less. As film thicknesses are reduced to achieve higher spatial resolution in the stack vertical direction, thickness uniformity becomes more important.

Figure 4:
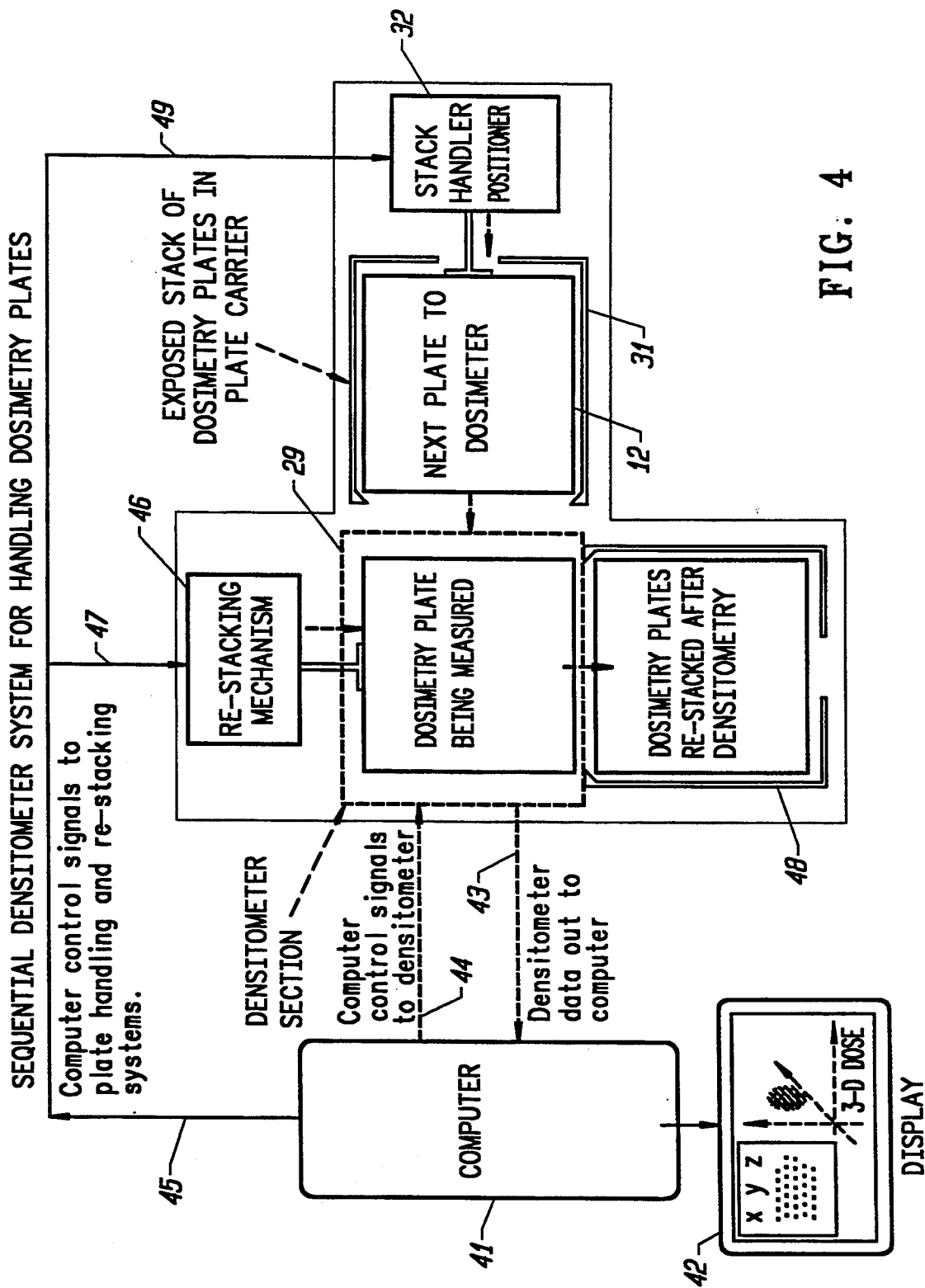
FIG. 4 depicts the control scheme according to the present invention.

FIG. 4 shows a more detailed schematic diagram of the stack handler and computer interaction. As discussed with respect to FIG. 2, once the stack has been exposed to radiation, the stack handler 32 ejects a film plate 29 from film stack 12 according to instructions received from computer 41. After the scanner 37 has scanned the image and sent the scanner output to the computer via wire or radio transmission means 43, the computer 41 sends computer control signals 44 and 45. Signal 44 is to control the densitometric functions of the scanner as needed. Signal 45 is controls the re-stacking mechanism 46 via transmission 47 such providing instructions to remove the film plate 29 from its scanning position and to stack it within frame 48. Computer control signals 45 also sends signal 49 to the stack handler positioner 32 to instruct it to move the next plate 29 into position for scanning by the scanner. This process is continuous until all of the plates have been scanned. Thus the scan data, that is, the optical density contours of each film is sent to the computer where they are stored and converted into gamma ray isodose contours so a computer program which produces calibration data and which reconstructs and displays the volumetric dose distribution may then compare the deposited dose to the desired dose.

The scanner of the present invention may be purchased through normal distribution channels or may be designed specifically to provide image date in accordance with the present invention. FIG. 5 shows the optical configuration of a scanner of the present invention. Light is generated from the source and is collimated through collimating lens 52, and in turn passes through one or more filters 53. The light projection then passes through film plate 29. A two-dimensional image of dosimetry plate 29 light transmission is focused by optical lens 54 onto the focal plane array detector 56 which is a pixel array. The detected image is then transmitted to the computer 41 for data reduction as described above. The scanner optical source and detector array are filterable to monitor only the chosen radiochromic optical band (e.g. typically at 670 nm for GAF-Chromic films and 605 nm for leucocyanide dyes in nylon film substrates), and a guard band (near 780 nm) that is unchanged by radiation.

As discussed above, there are many different types of film which can be used in accordance with the present invention depending upon the radiation wavelength generated by the testing apparatus. In each case, the film plates should be sufficiently rigid in order for the scanner to handle them at an accelerated rate. Thus, as shown in FIG. 6, another aspect of the present invention provides that a thin film of radiation sensitive material 58, the "sensitive layer," is formed on a substrate 59 which is between approximately 0.5 and five millimeters thick (neither of which is drawn to scale). The substrate material is transparent at the analytical wavelength of the film's sensitive layer (e.g. 605 or 670 nm). Moreover, the radiation response of the thin film layer and its substrate in terms of density (specific gravity), photon attenuation coefficient, and mass energy-absorption coefficient approximates that of the materials which make up human body tissue as closely as possible. Accordingly, it is preferable that the physical parameters of the substrate and the thin film layer are within ±10% (however, feasibly there could be up to approximately 25%) of those of the human tissue. Furthermore, it is suspected that the radiation applied to the substrate 59 has an effect on the ability of the thin film layer 58 to become exposed when radiation is applied thereto. Thus, the film plates according to the present invention should be positioned in the stack with the substrate material 59 in the path of the radiation beam 13 in front of the sensitive layer 58.

FIG. 7 shows one set of data from a three-dimensional x-ray dose measured by the film stack method of the present invention. A collimated x-ray beam 5 mm in diameter was programmed to generate an approximately spherical dose distribution 5 mm in diameter, in the center of the film stack. Under this investigation, the film layers were separated from one another by 3 mm thick plates of polystyrene, which has a radiation response similar to that of the human body. The exposure at the center of the film stack provided a spot that was 5.5 millimeter in diameter. The exposure on the film plates which were nine millimeters from the center of the stack was 17 millimeters across. Though not shown, the intensity of the exposures at the center were brighter than those at the edges of the stack. By adding the results of the exposure test together, a volume is generated indicating the regions which received exposure and their respective intensity levels. Thus, a model of the prescribed stereotaxic surgical maneuvers is generated and can be studied prior to the actual surgery on the human subject.

In accordance with the present invention, a convenient and simple to use system is provided for dosimetry. The stack handler of the present invention serves to increase the convenience and speed of data reduction. When the first film is read, its data is stored. When the second film is read, its data is assembled with that of the first film to create the first two layers of the three-dimensional picture. Therefore, the computer performs its tasks in parallel as each film is being read. Thus, when the last film is read, the computer is almost done with the three-dimensional distribution calculation. This process is substantially faster than reading out all of the films in one operation, and then computing the distribution. Moreover, the present invention is readily adaptable to computer data reduction and display methods. The number of films commercially available as described above also provide the ability for the present invention to be dose rate independent. The spatial resolution and position accuracy can be expected to be ±0.5 mm and the dose accuracy ±1% while being traceable to National Institute of Standards & Technology (NIST) standards. Moreover, the present invention is temperature and humidity independent within reasonable parameters. Furthermore, the films are typically stable after exposure so they can be maintained for further study, and as records.

What is claimed is:

1. A system for determining the radiation dosage distribution which is applied to a particular volume, comprising:
    a stack of individual films, each film responsive to said radiation to become exposed, said stack of films including said particular volume;
    means for applying focused radiation in a predefined direction so that said radiation passes through each of said films at a predefined location;
    means for controlling said radiation in a manner expected to produce a predefined exposure at said predefined location of each film;
    means for scanning said means for applying radiation so that radiation passes through each of said films at a plurality of predefined locations;
    means for inspecting said films to determine the exposure at each of said plurality of predefined locations for each of said films.

2. A system as recited in claim 1, wherein said means for inspecting further comprises a scanner for scanning each of said films and generating a scanner output, said scanner output comprising data representative of the actual radiation dosage at each of said plurality of predefined locations for each of said films.

3. A system as recited in claim 2, further comprising:
   data storage means for storing said scanner output and reference data representative of a desired radiation dose distribution of said particular volume; and
   comparison means for comparing said scanner output with said reference data.

4. A method for determining the radiation dosage distribution which is applied to a particular volume, comprising the steps of:
   providing a stack of individual films, each film responsive to said radiation to become exposed, said stack of films including said particular volume;
   applying focused radiation in a predefined direction so that said radiation passes through each of said films at a predefined location;
   controlling said radiation in a manner expected to produce a predefined exposure at said predefined location of each film;
   scanning said means for applying radiation so that radiation passes through each of said films at a plurality of predefined locations; and
   inspecting said films to determine the exposure at each of said plurality of predefined locations for each of said films.

5. A method as recited in claim 4, wherein said inspecting step further comprises the steps of:
   scanning each of said films with the scanner; and
   generating a scanner output, said scanner output comprising data representative of the actual radiation dosage at each of said plurality of predefined locations for each of said films.

6. A method as recited in claim 5, further comprising the steps of:
   storing said scanner output and reference data representative of a desired radiation dose distribution of said particular volume; and
   comprising said scanner output with said reference data.

7. A system for testing a model of the radiation dose to be applied to a particular volume of tissue, comprising:
   computer means for storing reference data representative of a desired radiation dose distribution of said particular volume of tissue;
   radiation application means for generating directable radiation;
   a stack of individual films positionable proximate said radiation application means for receiving focused radiation and thus becoming exposed;
   programming means for programming said radiation application means to scan said directable radiation over said stack of films;
   scanning means for scanning said exposed films and generating a scanner output, said scanner output providing data representative of the actual radiation dosage to which said films were subjected;
   transmission means for transmitting said scanner output to said computer means; and
   comparison means for comparing said scanner output with said stored data representative of said desired radiation dose distribution of said particular volume of tissue.

8. A system as recited in claim 7, wherein said stack of films is positioned in close proximity to said scanning means by a stack handler, said stack handler comprising:
   positioning means for holding each of said films securely in a stacked arrangement; and
   ejection means for individually ejecting each of said films into said scanning means.

9. A system as recited in claim 8, wherein said stack handler further comprises removing means for removing said films from said scanning means.

10. A system as recited in claim 7 wherein each of said individual films comprises a film plate including a radiation responsive thin film on a substrate which is between approximately one and three millimeters thick.

11. A system as recited in claim 7, wherein said reference data is stored by said computer means in digital form.

12. A system as recited in claim 7, wherein said scanner output is in digital form.

13. A system as recited in claim 7, wherein said comparison means generates a comparison signal and further comprising means for displaying said comparison signal.

14. A system as recited in claim 7, wherein said individual films are radiochromic films.

15. A method for testing a model of the radiation dose to be applied to a particular volume of tissue, said testing at least partially taking place within a testing apparatus including a radiation generating device, comprising the steps of:
   storing within a computer means reference data representative of a desired radiation dose distribution of said particular volume of tissue;
   generating directable radiation with said radiation generating device;
   providing a stack of individual films positionable within said testing apparatus for receiving focused radiation and thus becoming exposed;
   programming said radiation generating device to scan said directable radiation over said stack of films;
   scanning said exposed films with a scanner and generating a scanner output, said scanner output providing data representative of the actual radiation dosage to which said films were subjected;
   transmitting said scanner output to said computer means; and
   comparing said scanner output with said stored data representative of said desired radiation dose distribution of said particular volume of tissue.

16. A method as recited in claim 15, wherein said stack of films is positioned in close proximity to said scanner by a stack handler, said method further comprising the steps of:
   holding each of said films securely in a stacked arrangement within said stack handler; and
   individually ejecting each of said films from said stacked arrangement into said scanner.

17. A method as in claim 16, further comprising the step of removing said films from said scanner.

18. A method as recited in claim 15 wherein each of individual films comprises a film plate including a radiation responsive film on a substrate which is between approximately one and three millimeters thick.

19. A method as recited in claim 15, wherein said reference data is stored by said computer means in digital form.

20. A method as recited in claim 15, wherein said scanner output is in digital form.

21. A method as recited in claim 15, wherein said comparing step further comprises generating a comparison signal and said method further comprises the step of displaying said comparison signal.

22. A method as recited in claim 15, wherein said individual films are radiochromic films.

* * * * *